US006563129B1

United States Patent
Knobel

(10) Patent No.: US 6,563,129 B1
(45) Date of Patent: May 13, 2003

(54) METHOD AND DEVICE FOR THE CONTACTLESS MEASUREMENT OF THE DEFORMATION OF A SPECIMEN TO BE MEASURED

(75) Inventor: Bruno Knobel, Laufen (CH)

(73) Assignee: Zwick GmbH & Co, Ulm (DE)

( * ) Notice: Subject to any disclaimer, the term of this patent is extended or adjusted under 35 U.S.C. 154(b) by 0 days.

(21) Appl. No.: 09/643,371

(22) Filed: Aug. 22, 2000

(30) Foreign Application Priority Data

Aug. 25, 1999 (DE) .......................................... 199 40 217

(51) Int. Cl.⁷ .............................................. G01N 21/86
(52) U.S. Cl. ............................ 250/559.04; 250/559.05; 250/559.19; 356/603
(58) Field of Search ....................... 250/559.01–559.05, 250/559.19; 356/601, 603, 612, 620

(56) References Cited

U.S. PATENT DOCUMENTS

| | | | | | |
|---|---|---|---|---|---|
| 5,384,455 A | * | 1/1995 | Paxman | .................... | 250/201.9 |
| 5,568,259 A | * | 10/1996 | Kamegawa | .................. | 356/373 |
| 5,615,683 A | * | 4/1997 | Toge et al. | .................. | 128/666 |
| 5,757,473 A | * | 5/1998 | Kanduth et al. | .............. | 356/32 |
| 6,128,082 A | * | 10/2000 | Cloud | .......................... | 356/357 |
| 6,188,482 B1 | * | 2/2001 | Cloud | ......................... | 356/491 |
| 6,256,016 B1 | * | 7/2001 | Piot et al. | .................... | 345/166 |

FOREIGN PATENT DOCUMENTS

| | | |
|---|---|---|
| DE | 195 20 371 | 12/1996 |
| EP | 0 629 835 | 6/1994 |
| JP | 07004928 | 1/1995 |

* cited by examiner

*Primary Examiner*—Stephone B. Allen
*Assistant Examiner*—Christopher W. Glass
(74) *Attorney, Agent, or Firm*—collard & Roe, P.C.

(57) ABSTRACT

The invention relates to a method for measuring the deformation of a specimen without contact with the specimen. The surface of the measured specimen is partly illuminated by a laser light having uniform intensity. A speckle image is produced due to the local quality of the surface and is reproduced via an optical image sent onto a light-sensitive sensor. At least one reference speckle is selected by an evaluator unit from the totality of the speckles of the speckle image. The displacement of the reference speckle on the sensor is evaluated as the measure of the change that occurred in the specimen. In addition, the invention provides a device for performing this method.

19 Claims, 3 Drawing Sheets

METHOD AND DEVICE FOR THE CONTACTLESS MEASUREMENT OF THE DEFORMATION OF A SPECIMEN TO BE MEASURED

BACKGROUND OF THE INVENTION

1. Field of the Invention

The invention relates to a method for measuring the change in the shape of a specimen to be measured without making any contact with the specimen. In particular, this method is for measuring the change in the length of a specimen as the specimen is subjected to an external force.

2. The Prior Art

Methods for measuring the changes in length through speckle interferometry are known in the art. These methods are contact-free and involve the observation of markings on the specimen being measured. However, these known methods have two drawbacks in that there is an inadequate measuring range and take a long length of time because the numerical evaluation of the many individual speckles contributing to a speckle image requires a large expense and long computation time. Here, any displacement is computed by means of the cross correlation function between the speckle image recorded prior to the deformation of the tested specimen, and the speckle image measured in the course of the deformation of such specimen.

SUMMARY OF THE INVENTION

The invention is based on developing a method and a device to improve the time resolution and the spatial detection of the elongation of a specimen over large ranges.

The first part of the invention is a method for selecting at least one reference speckle using an evaluator unit from the totality of the speckles in the speckle image, and for tracking the displacement of the reference speckle to measure the change in length of the specimen.

By this method, the surface of the specimen being measured is partly illuminated with a laser light having uniform intensity. In addition, the speckle image is produced via an optical system on a sensor that is sensitive to light and is based on the local quality (or condition) of the surface.

In the field of material research and material testing, it is important to know how a specimen to be measured reacts with respect to a change in its shape, and to changes in the external conditions. For example, it is important to know how its length, width and thickness dimensions vary, due to a change in temperature, or how its dimensions change as the result of an external force acting on the specimen being measured. A particularly important test on the material is a tensile test. In this case, the measured specimen is tested in a tensile testing machine which measures the change in its length caused by a tensile force acting on the specimen. Because these tests are important, these tensile tests are standardized to compare the data taken in these tests.

For proper testing, it is best to first determine markings on the specimen. It is also best to observe any changes in the specimen without any contact on the specimen. Both requirements are satisfied by first acquiring speckle images. Speckle images are generated when an optically rough surface is illuminated with coherent light. In this case, the surface of most materials can be viewed as being rough in relation to the wavelength of the light used for the test. The speckle images are produced through constructive and destructive interference of phase-shifted, coherent wave packets that are reflected by different microscopic zones on the illuminated surface of the tested specimen. Speckle images, similar to a fingerprint, are a defined surface element, so that when such a surface element is shifted, the speckle images are displaced as well. These speckle images can be used as markings that are generated in a manner that does not require any contact.

The advantage of this method is that it reduces the data required for the evaluation of any change in length because at the start of the test, prior to the deformation of the measured specimen, a clearly distinguishable reference speckle is selected as a marking point from the total information contained in the speckle image. The reference speckle is detected by the sensor and only the movement of the reference speckle has to be subsequently observed. In addition, the method offers the advantage that the reference speckle is localized only on a small fraction of the entire surface of the sensor, so that the signals detected on the complementary surface of the sensor can remain unobserved, which means the signals will not overload the available computer capacity.

According to a preferred embodiment of the invention, a cluster of speckles from the totality of the speckles are used as the reference speckle. This method assures superior identification of the reference speckle even if the speckle image varies due to the deformation of the specimen being measured.

Furthermore, the measured specimen should be illuminated with a bar lighting element extending parallel to the direction in which the external force is acting. For example, the light should be designed as bar lighting having a greater expanse in one direction of the surface than in the other. The effect of such bar lighting is that surface area of the measured specimen generating the reference speckle moves in its direction of migration under constant lighting conditions. Thus, the surface areas of the measured specimen located outside of the direction of migration cannot influence the measured result by scattered light.

The sensor reading the light sent from the bar light is in the form of a line sensor extending along a single axis. The sensor is aligned parallel to the direction of action of the external force. The use of a line sensor, as opposed to a point-like (or punctiform) sensor, keeps the sensor from always having to be guided along with the motion of the reference speckle. This guided motion leads to distinct limitations of the measuring accuracy. As compared to the use of a matrix sensor, the use of a line sensor is better because a reduced amount of data is collected. This is because only the information disposed in the direction of movement of the reference speckle has to be evaluated via the speckle image.

This evaluation is particularly simple if the two-dimensional speckle image formed by the light that is reflected from the surface of the measured specimen is reproduced by the optical lens in the form of a one-dimensional representation of the speckle image. The area of a speckle image is changed to a bar-pattern in the transverse direction, and a typical bright-dark pattern is obtained as a result of the surface of the specimen being measured. Such a light-dark pattern can then be interpreted as a gray value image that is comparable to a bar code.

It is not necessary to evaluate the entire light-sensitive area of a sensor to observe the movement of a reference speckle. Thus, it is possible to select two or more reference speckles that are arranged spaced apart from each other, and then evaluate their displacement on the sensor. This method is an improvement over the prior art because the measurement of the longitudinal change occurring in a measured specimen subjected to tensile stress takes place in conformity with the standard even if only one sensor is used. This is because the sensor measures accuracy requirements. The relative motion of two markings moving along with the measured specimen can be accomplished with very high accuracy.

This high accuracy is available across the entire measuring range, with the measuring range being limited only by the dimension of the sensor. To overcome this limitation, and to expand the measuring range, with reduced measuring accuracy, the position of the reference speckle is put in relation to the limits of the sensor by the evaluator unit. This reduced measuring accuracy is no longer critical because these measurements occur after the start of the measurements of the specimen. The position of the reference speckle is kept within the measuring range by a slaving unit which is normally void when a transgression is expected to occur beyond the measuring range preset by the limits of the sensor. It is possible to use the slaving unit such that it turns the optical lens wherein the corresponding angle of rotation is sent to the evaluator unit. Alternatively, the sensor can be linearly adjusted by the slaving unit wherein the corresponding distance of displacement is transmitted to the evaluator unit.

For the slaving unit to operate as smoothly and uniformly as possible, there is an evaluator unit that evaluates the trajectory of the reference speckle in real time for prognosticating its position. The evaluator unit then transmits the prognosis to the slaving unit for the purpose of positioning the reference speckle in relation to the sensor within the measuring range of the latter.

To measure the change in length of a specimen, it is possible to reproduce on two separate sensors, via two separate optical lenses, two reference speckles originating from two surface areas that are arranged spaced apart from one another on the specimen to be measured. These two reference speckles are selected and evaluated by the evaluator unit. In addition, the use of two sensors at the same time offers the advantage that the measuring range grows larger until the slaving unit has to be activated to expand the measuring range further.

The invention also provides a device consisting of a laser that illuminates the surface of the specimen to be measured. In addition, the optical system reproduces the speckle image generated by the illumination on a light-sensitive sensor. There is also an evaluator unit that selects at least one reference speckle from the speckle image reproduced on the sensor, and evaluates the displacement of the reference speckle. In one embodiment of the device, the optical system has a cylinder lens. In an alternative embodiment of the invention, the optical system is a Fourier shutter. Both the cylinder lens and the Fourier shutter transform the two-dimensional speckle image into a one-dimensional representation of the speckle image in the form of a gray-value image. The image can be received and subsequently interpreted in a simple way by the line sensor.

To increase the measuring accuracy and avoid adjustment problems, the laser, the optical lens, and the sensor are integrated in a single measuring head. To expand the measuring range, a slaving unit is associated with the measuring head to position the sensor in the expected location of the reference speckle. The slaving unit is connected to the evaluator unit via a data transmission line. This design measures both the change in the position of the reference speckle on the sensor and the change in the position of the sensor itself which increases the accuracy of quantifying the deformation of the specimen.

To conform the measurements to the industry standard and to expand the measuring range, the device is designed to have two measuring heads for measuring the change in the position of two reference speckles. The latter design originates from two surface zones that are arranged on the specimen being measured spaced apart from each other. The sensor is formed by a CCD-sensor or alternatively by any other electro optical sensors (e.g. an active pixel sensor (APS)).

The speckle image reproduced on the sensor is transmitted to the sensor so that optimal spatial resolution is possible. In addition to suitable enlargement, the pixel sizes are adapted to the speckle image.

DETAILED DESCRIPTION OF THE PREFERRED EMBODIMENT

Figure 1:
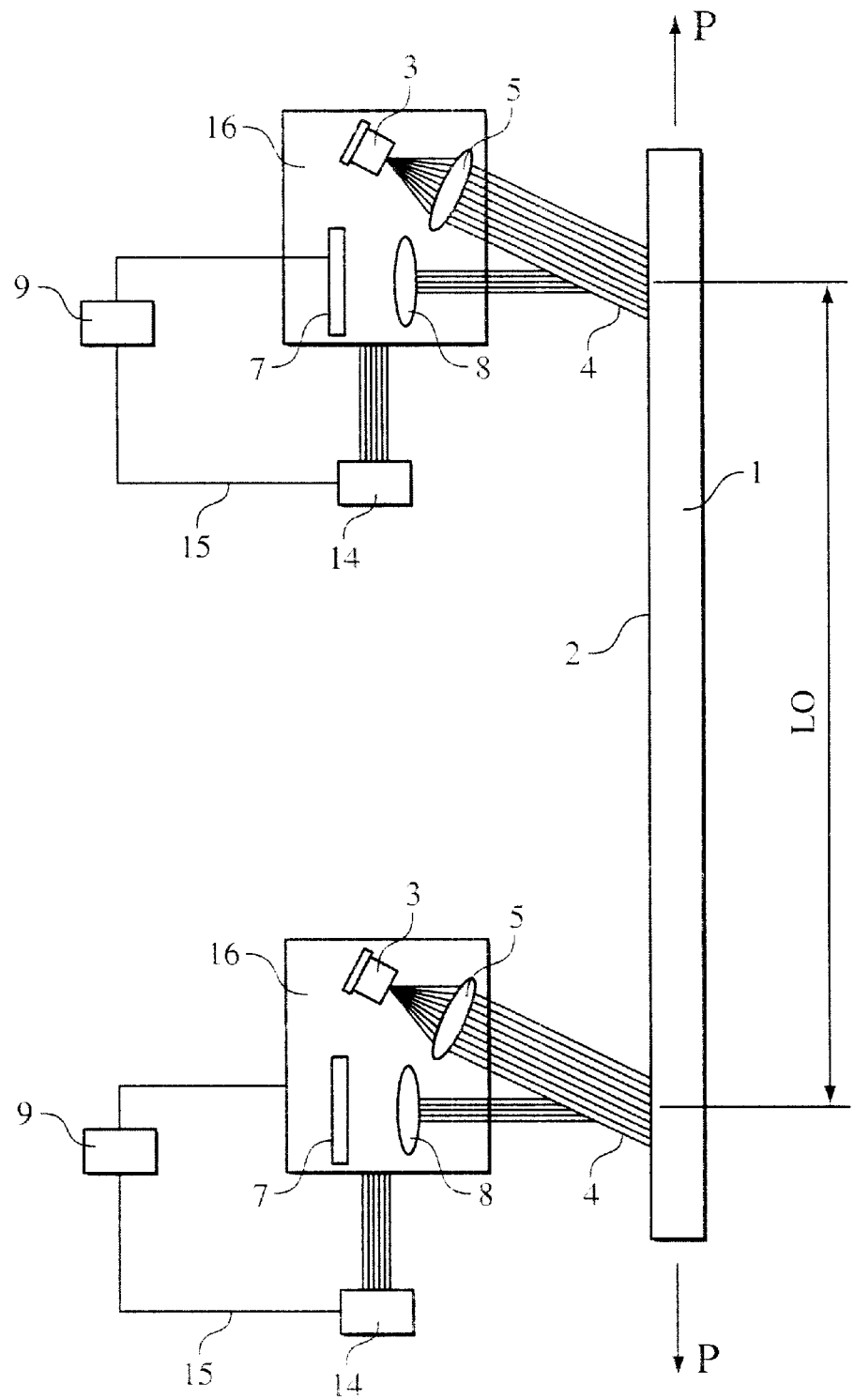
FIG. 1 is a schematic representation of the device for contactless measurement of the deformation of a specimen using speckles for the measurement.

Referring to FIG. 1, there is shown a device for the contactless measurement of the deformation of a measured specimen 1. The device is designed to carry out tensile tests. Tensile tests change the length of specimen 1 due to an external tensile force. The tensile force is symbolized by the arrows "P". The change in length was formerly measured by high time and location resolution. To measure the change in length over time, the change occurring in the measured starting length $L_0$ is observed, wherein the initial length is preset on the measured specimen 1 by two markings 6. Each of two markings 6 is provided by a speckle image 11 that is generated on surface 2 of measured specimen 1 without contact. To generate speckle image 11, the device has a laser 3 that exposes a substantially one-dimensional bar 4, on the surface 2 of measured specimen 1 using a laser light of constant intensity. Bar illumination 4 is generated by a lens system 5.

Figure 2:
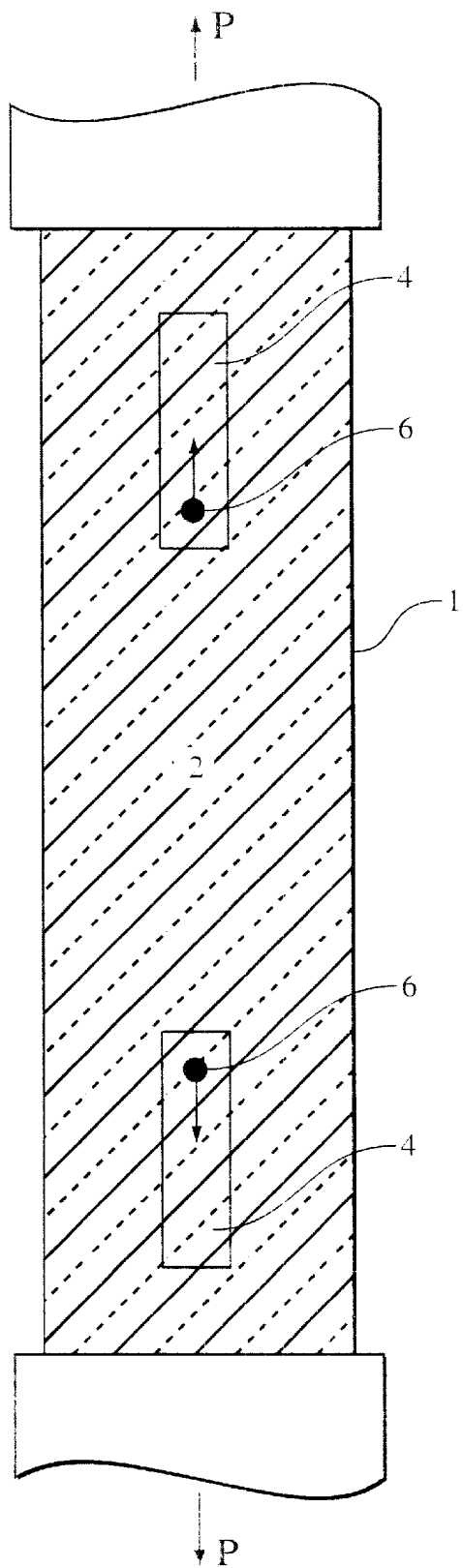
FIG. 2 is a top view of the specimen with two parts of the surface being illuminated by bar lighting.

Since specimen 1 being measured has an optically rough surface 2, speckle images 10 are generated by the coherent and collimated light of laser 3. Speckle images 10 are each characteristic of a point spaced apart on an interval or bar illumination 4. In this case, these points function as marking 6. Speckle image 10 of the applied bar illumination 4, is reproduced by an optical lens 8 sent to a sensor 7 that is sensitive to light. An evaluator unit 9 selects a clearly distinguishable reference speckle 11 from the totality of the speckles of the speckle image 10 and follows this speckle as shown in FIG. 2. Reference speckle 11 moves in the presence of a change in length of measured specimen 1 within the interval located in bar illumination 4. Based on a change in the location of reference speckle 11, on sensor 7, it is possible to directly infer the change in length of marking 6.

If, as shown in FIG. 1, there is observed a simultaneous change in the position of two points of surface 2 of measured specimen 1, the instantaneously measured length deviating from the initially measured length $L_0$ is obtained in conformity with the industry standard.

Figure 3A:
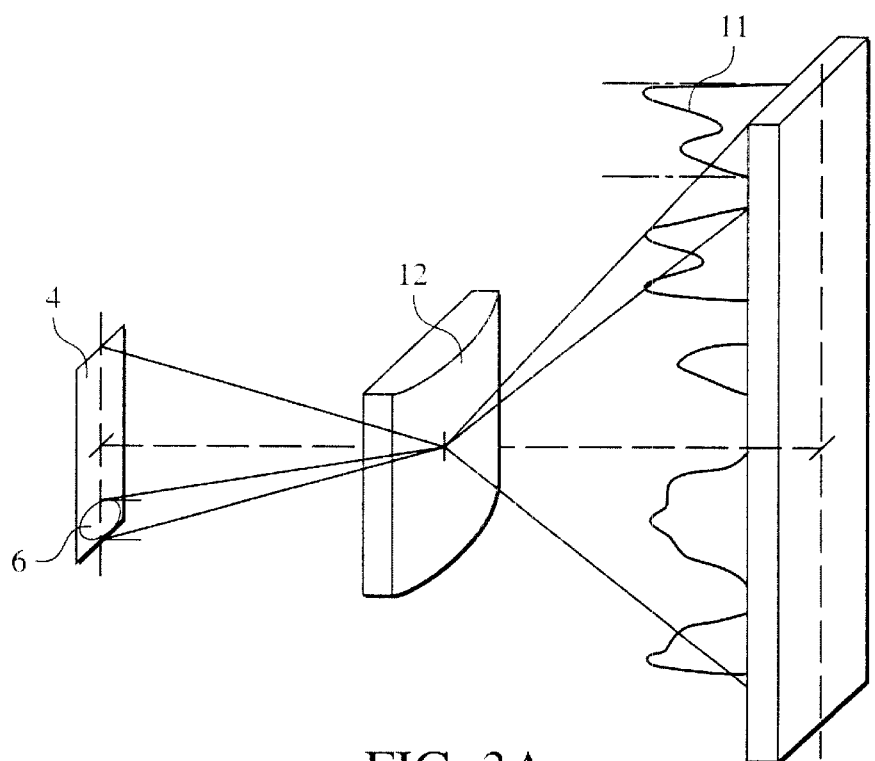
FIG. 3A is a schematic representation of the reproduction of the speckle image on the sensor, and the selection of a reference speckle by the evaluator unit.
Figure 3B:
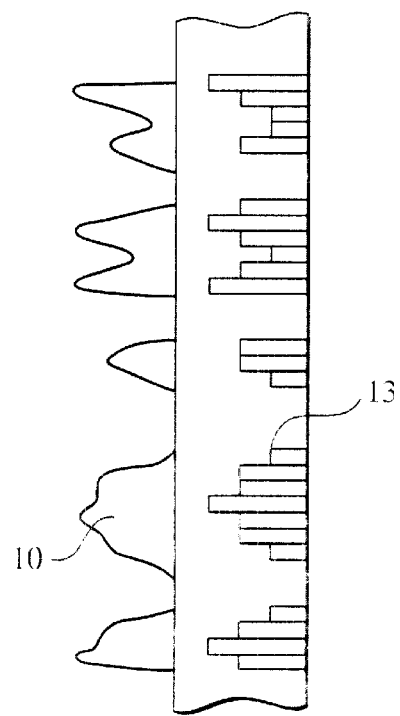
FIG. 3B is a schematic representation of the reproduction of the speckle image on the sensor, and a selection of the reference speckle by the evaluator unit.

As shown in FIG. 3A, Optical lens 8 can contain either a cylinder lens 12 or a Fourier shutter. These two devices both have properties for transforming two-dimensional speckle image 10 shown in FIG. 3B into a one-dimensional representation of speckle image 10. Here, a reference speckle 11 is shined on through cylinder lens 12 and on to a bar illumination 4 to measure the change in length of marking 6. This transformation results in a gray-value image 13 that is schematically shown in FIG. 3B. Gray-value image 13 can be interpreted by evaluator unit 9 in a simple way and relatively quickly.

In addition, as shown in FIG. 1 evaluator unit 9 determines reference speckle 11, which is selected from a cluster of speckles taken all of the speckles. Evaluator unit 9 then evaluates the change in the position of reference speckle 11 (FIG. 3A).

The change in the position of reference speckle 11 takes place in the direction in which the tensile force is acting. Thus, sensor 7 is designed only in the form of a line sensor and is typically realized in the form of a CCD-sensor or APS-sensor.

The measuring range for measuring the change in length of measured specimen 1 is limited only by the optical system employed, and by the length of sensor 7 and the lens fitting the system. When two sensors 7 are used as shown in FIG. 1 for determining the initial (or starting) length $L_0$, the change in length of measured specimen 1 can reach two times the length of sensor 7. This use of two sensors assures that the measurement can be carried out with high accuracy.

If the measuring range is not adequate, an evaluator unit 9 will set the reference position speckle 11 in relation to optical lens 8. This occurs if the measuring range preset by the limits of sensor 7 is expected to be exceeded. The reference position speckle 11 is kept within the measuring range by a slaving unit 14. It is also possible to use the slaving unit to turn measuring head 16 and then transmit the corresponding angle of rotation to the evaluator unit via a data transmission line 15, or to adjust measuring head 16 linearly and to transmit the distance of displacement to evaluator unit 9.

Since reference position speckle 11 migrates in a constant way, the evaluator unit 11 is capable of interpreting the trajectory of reference position speckle 11 to determine its position. The information is transmitted to a slaving or trailing unit 14, so that it always positions reference position speckle 11 in relation to sensor 7 within the measuring range of this sensor.

FIG. 1 also shows laser 3, optical lens 8 and sensor 7 being integrated in a measuring head 16, in which a total of two measuring heads are present.

Accordingly, while a few embodiments of the present invention have been shown and described, it is to be understood that many changes and modifications may be made thereunto without departing from the spirit and scope of the invention as defined in the appended claims.

What is claimed is:

1. A method for the contactless measurement of change in a spacial shape of a measured sample to measure the change in length of the measured sample, the method comprising the steps of:
   a) illuminating a surface of a measured sample with uniform intensity with laser light and a speckle image;
   b) reproducing a sample image via optics on a light sensitive sensor;
   c) selecting a cluster of speckles as a reference speckle from a totality of said speckles in said speckle image by using an evaluation unit;
   d) evaluating a displacement of said reference speckle; and
   e) positioning said sensor in relation to said reference speckle using a slaving unit to move said sensor to focus said sensor on said reference speckle.

2. The method according to claim 1, wherein the step of selecting at least one reference speckle includes selecting a cluster of speckles for use as said reference speckle from said speckle image.

3. The method according to claim 1, wherein said step of partially illuminating the specimen includes illuminating with a bar light that extends parallel to the direction in which an external force is acting.

4. The method according to claim 1, wherein said step of reproducing said speckle image includes using a sensor in the form of a one-dimensionally extending line sensor, said line sensor being aligned parallel with the direction in which the external force is acting.

5. The method according to claim 1, wherein the step of reproducing said speckle image comprises reproducing said two-dimensional speckle image formed by light reflected by said surface of the measured specimen in the form of a one-dimensional representation of said speckle image.

6. The method according to claim 1, wherein said step of selecting at least one reference speckle comprises selecting two of said several reference speckles arranged with a spacing from each other and evaluating their displacement on the sensor.

7. The method according to claim 1, further comprising the step of turning a measuring head by using said slaving unit wherein said angle of rotation is transmitted to said evaluator unit.

8. The method according to claim 1, further comprising the step of linearly adjusting a measuring head by using a trailing unit wherein a distance of displacement is transmitted to said evaluator unit.

9. The method according to claim 1, further comprising the step of evaluating the trajectory of said reference speckle by using an evaluator unit for determining the position of said reference speckle, and transmitting this position to said slaving unit for positioning said reference speckle in relation to said sensor within the measuring range.

10. The method according to claim 1, further comprising the step of reproducing two reference speckles originating from two surface zones arranged spaced-apart on the measured specimen by using two separate sensors via a set of two separate optical lens, wherein these two reference speckles are selected and evaluated by said evaluator unit.

11. A device for illuminating a surface of a measured sample with uniform intensity with laser light and a speckle image, wherein the device reproduces a sample image, selects a cluster of speckles as a reference speckle from a totality of the speckles in the speckle image, and evaluates a displacement of the reference speckle, the device comprising:
   a) a laser for illuminating the surface of the measured sample;
   b) optics for reproducing a speckle image developed by illumination;
   c) a light sensitive sensor for receiving said image from the optics;
   d) an evaluation unit which selects from the speckle image at least one cluster of speckles as the reference speckle; and e) at least one slaving unit in communication with said evaluation unit, said slaving unit for moving and positioning said light sensitive sensor in a position of said reference speckle to be viewed.

12. The device according to claim 11, wherein said optical system further comprises a cylindrical lens.

13. The device according to claim 11, wherein said optical lens further-comprises a Fourier shutter.

14. The device according to claim 11, wherein said sensor is designed as a line sensor.

15. The device according to claim 11, wherein said laser, said optical lens and said sensor are integrated in a measuring head.

16. The device according to claim 15, wherein said at least one slaving unit is for positioning said sensor in an expected position of said reference speckle; and wherein said slaving unit is connected with said evaluator unit via a data transmission line.

17. The device according to claim 16, further comprising at least one additional measuring head for measuring a change in a position of said two reference speckles, said reference speckles originating from a set of two surface zones arranged spaced apart from each other on the measured specimen.

18. The device according to claim 11, wherein said sensor is formed by a CCD-sensor.

19. The device according to claim 11, wherein said sensor is formed by an APS-sensor.

* * * * *